United States Patent
Yokota et al.

(10) Patent No.: US 6,200,445 B1
(45) Date of Patent: Mar. 13, 2001

(54) SULFUR DIOXIDE GAS SENSOR

(75) Inventors: Minoru Yokota, Okazaki; Takao Murase, Konan, both of (JP)

(73) Assignee: NGK Insulators, Ltd. (JP)

( * ) Notice: Subject to any disclaimer, the term of this patent is extended or adjusted under 35 U.S.C. 154(b) by 0 days.

(21) Appl. No.: 09/198,612

(22) Filed: Nov. 24, 1998

(30) Foreign Application Priority Data

Dec. 1, 1997 (JP) .................................. 9-330503
Nov. 10, 1998 (JP) ................................ 10-319561

(51) Int. Cl.$^7$ .................................. G01N 27/407
(52) U.S. Cl. .................. 204/424; 204/291; 204/292; 204/293; 204/412; 204/425; 204/426; 204/427; 205/784.5; 205/786.5
(58) Field of Search .................. 204/291–293, 204/421–429; 205/783.5–785, 786.5

(56) References Cited

U.S. PATENT DOCUMENTS

| | | | |
|---|---|---|---|
| 3,914,169 | * 10/1975 | Horowitz | 204/427 |
| 4,224,113 | * 9/1980 | Kimura et al. | 204/426 |
| 4,502,939 | * 3/1985 | Holfelder et al. | 204/428 |
| 4,514,277 | * 4/1985 | Sakurai et al. | 204/424 |
| 4,976,991 | 12/1990 | Ammende et al. | |
| 5,766,433 | * 6/1998 | Can et al. | 204/426 |

FOREIGN PATENT DOCUMENTS

| | | |
|---|---|---|
| 0 798 556 A2 | 10/1997 | (EP) . |
| WO 97/42495 | 11/1997 | (WO) . |

* cited by examiner

Primary Examiner—T. Tung
(74) Attorney, Agent, or Firm—Parkhurst & Wendel, L.L.P.

(57) ABSTRACT

A sulfur dioxide gas sensor having a high selectivity of $SO_2$ gas, and an operability at a high temperature which comprises: a solid electrolyte having oxygen ion conductivity; a detecting electrode for measuring sulfur dioxide gas, electrically connected to at least a part of a surface of the solid electrolyte and containing glass and either gold or a gold alloy; and a basic electrode for measuring sulfur dioxide gas, electrically connected to at least a part of a surface of the solid electrolyte and containing Pt.

18 Claims, 8 Drawing Sheets

SULFUR DIOXIDE GAS SENSOR

BACKGROUND OF THE INVENTION AND RELATED ART STATEMENT

The present invention relates to an $SO_2$ gas sensor for measuring the sulfur dioxide ($SO_2$) gas concentration in the exhaust gas of a combustion engine, or the like, or in the air. Particularly, the present invention relates to a $SO_2$ gas sensor which can reduce the influence of coexistent oxygen ($O^2$) on a value obtained by a $SO_2$ gas measurement and which can operate even at such a high temperatures as 600° C. 900° C.

In boilers for thermal power generation or incineration facilities, there are emission standards on toxic gases that occur in the exhaust gas, such as $NO_x$ and $SO_2$, which exist for environment protection. Each facility is required to monitor the concentration of these toxic gases in order to prove that the standards are being followed. In thermoelectric power plants or incineration facilities, there is used a measuring apparatus of a nondispersive infrared ray absorption type (NDIR type) to monitor these air-pollutive gases. Since the measuring apparatus is not directly inserted into the exhaust gas, the exhaust gas is sampled by an absorption pump and analyzed in a place separate from the passage for the exhaust gas.

However, in the NDIR type of measuring apparatus, a sampling apparatus is exposed to high temperatures. Therefore, it requires rather frequent maintenance checks, which because of various restrictions are difficult to carry out without stopping the operation of the boiler or the incineration facilities.

Further, the apparatus itself must have gas-pretreatment portions for removing dust and water contained in an exhaust gas, which in combination with the use of an absorption pump, inevitably enlarges the apparatus and raises its price.

Furthermore, because a measurement of the concentration of toxic gases such as $SO_2$ in an exhaust gas requires the absorption step by the use of an absorption pump, even when such a concentration in an exhaust gas reaches nearly a critical level by, for example, an unexpected extraordinariness of combustion facilities; it is difficult to avoid delay in a response time, and a certain time lag is necessary to cope with the extraordinariness, or the like, which increases the risk of an unexpected accident.

Additionally, since the sensor used in the apparatus sustains interference of $CO_2$, hydrocarbons inevitably discharged into an exhaust gas, or the like, a precise measurement cannot be expected.

The other methods for measurement shown in JIS B7981 are (1) an electrolytic conductivity method, (2) an ultraviolet ray absorption method, and (3) controlled potential electrolysis. However, these methods have problems regarding sampling due to the aforementioned nondispersive infrared ray absorption, and each of these methods is influenced by peculiar interferential gases.

SUMMARY OF THE INVENTION

The present invention was made in view of the aforementioned problems and provides a $SO_2$ gas sensor for appropriately measuring a concentration of $SO_2$ gas contained in an exhaust gas from thermoelectric power plants or incineration facilities and further provides a $SO_2$ gas concentration measuring apparatus using the $SO_2$ gas sensor.

According to the present invention, there is provided a sulfur dioxide gas sensor comprising:

a solid electrolyte having oxygen ion conductivity;

a detecting electrode for measuring sulfur dioxide gas, electrically connected to at least a part of a surface of the solid electrolyte; and a basic electrode for measuring sulfur dioxide gas, electrically connected to at least a part of a surface of said solid electrolyte;

wherein the detecting electrode contains glass and either gold or a gold alloy.

According to the present invention, there is further provided a sulfur dioxide gas sensor comprising:

a solid electrolyte having oxygen ion conductivity;

a detecting electrode for measuring sulfur dioxide gas, electrically connected to at least a part of a surface of the solid electrolyte;

a basic electrode for measuring sulfur dioxide gas, electrically connected to at least a part of a surface of the solid electrolyte; and a detecting electrode for measuring oxygen and/or a basic electrode for measuring oxygen;

wherein the detecting electrode for measuring sulfur dioxide gas contains glass and either gold or a gold alloy.

According to the present invention, there is also provided an apparatus for measuring said $SO_2$ gas equipped with said sensor.

According to the present invention, there is furthermore provided a sulfur dioxide gas sensor comprising:

a solid electrolyte having oxygen ion conductivity;

a detecting electrode for measuring sulfur dioxide gas, electrically connected to at least a part of a surface of the solid electrolyte;

a basic electrode for measuring sulfur dioxide gas, electrically connected to at least a part of a surface of the solid electrolyte;

a detecting electrode for measuring oxygen and/or a basic electrode for measuring oxygen; and an oxygen pump cell for controlling oxygen content in the atmosphere to be measured;

wherein the detecting electrode for measuring sulfur dioxide gas contains glass and either gold or a gold alloy.

It is preferable that the electrode used for the oxygen pump cell in said $SO_2$ gas sensor is made of a metal oxide, which does not oxidize $SO_2$ gas.

Preferably, the $SO_2$ gas sensor has a gas diffusion rate-determining layer on a surface of the detecting electrode. The sensor may have a structure in which both the detecting electrode for measuring $SO_2$ gas and the basic electrode for measuring $SO_2$ gas are disposed on the same surface of the solid electrolyte. Further, the sensor may have a three-electrode structure in which a reference electrode for measuring $SO_2$ gas is employed next to the detecting electrode for measuring $SO_2$ gas and the basic electrode for measuring $SO_2$ gas.

A $SO_2$ gas sensor of the present invention employs a method of measuring a change of electromotive force caused by adsorption/oxidation of sulfur dioxide gas in the detecting electrode for measuring $SO_2$ gas when a certain current is applied between the detecting electrode and the basic electrode for measuring $SO_2$. This enables improvement of $SO_2$ detection sensitivity.

Alternatively, an $SO_2$ gas sensor of the present invention may employ a method in which a $SO_2$ gas concentration is measured by measuring the change of amperage caused by an oxidation reaction of $SO_2$ gas on the detecting electrode for measuring $SO_2$ gas when the voltage is kept constant between the detecting electrode for measuring sulfur dioxide and the basic electrode for measuring sulfur dioxide. This also enables improvement of $SO_2$ detection sensitivity and assists in conduction of excellent measurement of concentration.

A $SO_2$ gas sensor of the present invention having electrodes for measuring oxygen, which are separate from the electrodes for measuring $SO_2$, employs a method in which a $SO_2$ gas concentration and an oxygen concentration are measured simultaneously, and the $SO_2$ gas concentration is amended according to the results of the measurement of the oxygen concentration.

In the $SO_2$ gas sensor of the present invention having a reference electrode for measuring oxygen, which are seperate from the electrodes for measuring $SO_2$, a certain current is applied between the detecting electrode and the basic electrode for measuring $SO_2$ gas and the voltage between the reference electrode and the detecting electrode is measured, or a current between the detecting electrode and the reference electrode is measured by keeping the voltage constant between the detecting electrode and the reference electrode. This enables measurement with high precision by separating only the reaction of $SO_2$ gas on the detecting electrode. Therefore, in the present invention, it is possible to improve measurement precision by combining the aforementioned methods with the function of the structure of the $SO_2$ gas sensor.

It is preferable that a solid electrolyte, which is one of the members constituting the aforementioned $SO_2$ gas sensor, contains zirconium oxide and a stabilizer. As a stabilizer, there can be suitably used magnesium oxide, calcium oxide, yttrium oxide, cerium oxide, scandium oxide, and a rare earth metal oxide. For electrodes except for the detecting element for measuring $SO_2$ gas, it is preferable to use a cermet electrode made of porous platinum or a mixture of porous platinum and the same material as the solid electrolyte. When the gas sensor has a structure in which the solid electrolyte can be heated and maintained at a constant temperature of 600° C. to 900° C., by using an element for measuring temperature and a heater installed on the vicinity of solid electrolyte or those installed unitarily with the solid electrolyte, it can cope with a decrease in temperature dependency of a value obtained by the measurement.

When the detecting electrode for measuring $SO_2$ gas is formed on the solid electrolyte, the solid electrolyte is roughened as shown in FIG. 13 by subjecting the solid electrolyte to chemical etching or the like in advance so as to enhance adhesion between the solid electrolyte and the detecting electrode. Additionally, $SO_2$ gas detection sensitivity gas is further improved by increasing the area of contact interfaces among the detecting element, the solid electrolyte, and $SO_2$ gas.

The same effect can be obtained by disposing an electrode film on a layer which is disposed on the solid electrolyte and contains Au or Au alloy fine particles having a certain average diameter.

According to the present invention, in an apparatus for measuring the gas component concentration in an exhaust gas, $SO_2$ concentration can be measured more precisely by using the aforementioned oxygen gas sensor as a direct inserted type or a direct coupled type of sensor, resulting in more precise control of $SO_2$ concentration in an exhaust gas. The direct insert type of sensor is disclosed by Japanese Patent Laid-Open 1-250753, where the sensor is directly inserted into a measurement atmosphere. The direct coupled type of sensor is disclosed by Japanese Patent Laid-Open 3-277957, where the sensor is disposed in a periphery of a measurement atmosphere and takes the gas to be measured into the apparatus by using the flow speed of the gas to be measured.

As described above, the present invention employs, as a detecting electrode for measuring $SO_2$ gas concentration, an electrode made of metallic material such as gold or a gold alloy, which has lower catalytic ability than platinum (which has conventionally been used), and a glass component (for when $SO_2$ gas concentration in a combustion engine or in the air is measured). This enables a reduction in the influence of $O_2$ concentration on a value of $SO_2$ gas concentration and raises the operation temperature of the sensor up to 600° C.–900° C.

An oxidation reaction of $SO_2$ gas is accelerated in a detecting electrode by applying a certain current between he detecting electrode for measuring $SO_2$ gas and the basic electrode for measuring $SO_2$ gas, or by keeping the voltage between the detecting electrode and the basic electrode constant, thereby improving sensitivity of the $SO_2$ gas sensor to $SO_2$ gas.

DETAILED DESCRIPTION OF THE PREFERRED EMBODIMENT

The present invention is described on the basis of the preferred embodiments with reference to drawings. However, the present invention is by no means limited to these embodiments.

Figure 1:
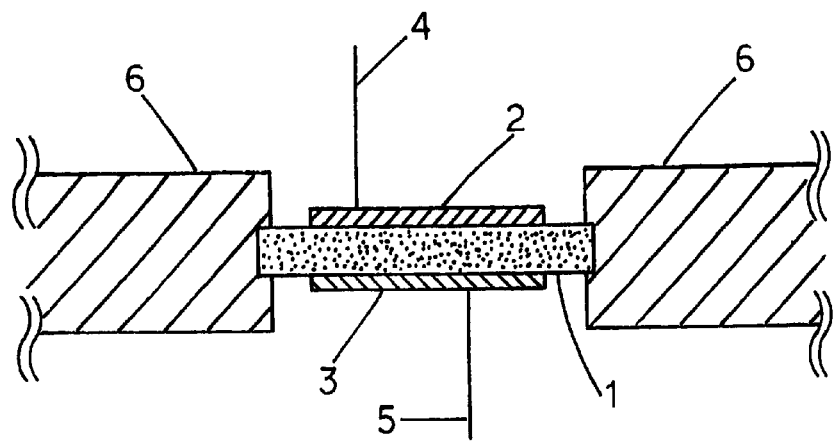
FIG. 1 is a sectional view showing a basic structure of a $SO_2$ gas sensor of the present invention.

FIG. 1 is a sectional view showing the basic structure of a $SO_2$ gas sensor of the present invention. A basic electrode 2 and a detecting electrode 3, which are a pair of electrodes, are formed on each of the surfaces of a solid electrolyte plate 1 so as to sandwich the solid electrolyte plate 1. The basic electrode 2 is formed in the side of basic gas, and the detecting electrode 3 is formed in the side of gas to be measured. Leads 4 and 5 are connected to the basic electrode 2 and the detecting electrode 3, respectively. The solid electrolyte plate 1 is engaged with substrate 6 and serves as a partition between the gas to be measured and the standard gas.

The solid electrolyte plate 1 may be made of any material as long as it has oxygen ion conductivity, such as zirconium oxide, bismuth oxide, or cerium oxide. The present invention preferably employs stabilized zirconia, which is excellent in high temperature stability and chemical stability. The term "stabilized zirconia" means a product whose cubic crystal which is a stabilized phase of zirconium oxide at a high temperature is stabilized at all range of temperatures so as to prevent a martensite-type phase transition. This is done by forming a solid solution with a divalent or trivalent metal oxide, which is called a stabilizer since pure zirconium oxide causes the phase transition at about 1000° C. due to a charge in volume between the monochrinic crystal and the tetragonal crystal thereof, which results in the formation of cracks. The solid solution of such a stabilizer generates an oxygen defect and improves conductivity. As a stabilizer in the present invention, there can be suitably used magnesium oxide (MgO), calcium oxide (CaO), yttrium oxide ($Y_2O_3$), cerium oxide ($CeO_2$), scandium oxide ($Sc_2O_3$), and rare earth oxides.

The solid electrolyte plate 1 is produced by subjecting a green sheet obtained by a known method such as press molding, slip casting, extrusion molding, and doctor blading then punching to obtain a compact having a predetermined shape, removing the binder, and firing. As necessary, it is further subjected to grinding and/or sanding to obtain a sample plate.

Then, the basic electrode 2 is to be electrically connected with a solid electrolyte plate 1. Since the basic electrode 2 is required to serve as an electrode for diffusing/adsorbing a gas, it is preferable for this electrode to be porous. Since the basic electrode 2 is the place for an electrochemical reaction when $O_2$ in a standard gas is ionized, there is suitably used Pt, which has a characteristic of adsorbing and ionizing $O_2$, as a material for the basic electrode 2. Alternatively, an alloy containing Pt as a main component and Pd, Rd, or the like, or Pt, or a cermet material composed of a Pt alloy and a solid electrolyte material may be used. The reason why a cermet is used as a material for a basic electrode 2 is that it provides many places for the electrochemical reaction and avoids exfoliation, or the like, of the electrode caused by a thermal stress which occurs at high temperatures. It also aims at improvement of adhesion between the electrode and the solid electrolyte and adjustment of the coefficient of thermal expansion since the electrochemical reaction of ionizing $O_2$ in the standard gas takes place at the interfaces among the three phrases of the gas phase, the metallic electrode, and the solid electrolyte.

The basic electrode 2 is fixed to the solid electrolyte plate 1 by printing a paste made of a cermet of Pt and a solid electrolyte on a surface of a solid electrolyte plate 1 by a method such as screen printing, abutting a Pt mesh to the paste before it is dried, and baking by drying it. Alternatively, there may be employed a method in which a Pt mesh is impregnated with a slurry containing Pt, the Pt mesh is placed on the solid electrolyte plate 1 before the slurry is dried, and they are subjected to baking. These methods are simplest and easiest. Alternatively, the paste may be left unbaked after the screen printing. The baking may be performed simultaneously with the baking of the detecting electrode, which is formed on the surface of the solid electrolyte 1, opposite to the basic electrode 2. Alternatively, the baking of the basic electrode 2 may be performed separately from the baking of the detecting electrode 3. Regarding fixation of the Pt lead 4 to the basic electrode, when the basic electrode is Pt mesh, it is preferable that the Pt lead 4 has previously been welded to the Pt mesh by spot welding, arc welding, or the like, so as to give it high strength in fixation. When only a screen printing is employed for forming an electrode, the Pt lead 4 can be fixed by baking. Alternatively, the electrode may be found by Pt plating, baking of chloroplatinic film, or the like.

On the other hand, a detecting electrode 3 is disposed on the surface, opposite to the basic electrode 2, of the solid electrolyte plate 1. The detection electrode 3 is preferably porous since, as a result of an oxidative reaction between an oxygen ion transferred through the solid electrode and $SO_3$ gas absorbed in the metallic component of the electrode, a function, which on interface between the gas phase, the metallic electrode and the solid electrode, and which is capable of liberating $SO_2$ gas, is necessary. A material suitable for the detecting electrode 3 preferably has the characteristic of not promoting oxidation of $SO_2$ gas by coexisting $O_2$. That is, it is preferable that a reaction of an adsorbed oxygen (O(ad)) and $SO_2$ gas, as shown in the following formula 1, is not caused and that an electron ($e^-$) is generated by the reaction of an oxygen ion ($O^{2-}$) which transferred in a solid electrolyte from the side of the basic electrode and $SO_2$ gas, as shown in the following formula 2. This electron is applied to a $SO_2$ gas measurement.

$SO_2 + O(ad) \; SO_3$                                   [Formula 1]

$SO_2 + O^{2-} \; SO_3 + 2e^-$                          Formula 2

From the above, gold (Au) is suitably used as a metal for the detecting electrode in the present invention. It is more preferable to employ an Au alloy in which 1–10 wt % of another noble metal is added to Au. By adding, to Au, another noble metal of 0.1–10 wt %, preferably 0.1–5 wt %, more preferably 0.1–1 wt %, aggregation of Au particles at a high temperature upon producing the detecting electrode is suppressed, which enables maintenance of the porosity and enlarge the surface area of the detecting electrode. As a result, the sensitivity with which $SO_2$ is detected can be improved.

Incidentally, Rh, Pt, Pd, Ag, or the like, may be used as a metal to be alloyed with Au. Au concentration is 90 wt % or more, preferably 95 wt % or more, more preferably 99 wt % or more. Au concentration is suitably determined depending on the alloys melting point and baking temperature, or depending on the temperature at which the sensor is used.

There can be suitably used a cermet electrode in which the same material as the solid electrolyte plate is mixed with Au or a Au alloy. The reason why a cermet material is used is the same as the case of the basic electrode 2.

In the case where a layer of Au or fine particles from an Au alloy are formed on the electrolyte and an electrode film is formed on the layer so as to obtain the detecting electrode, a paste in which fine particles are dispersed is applied on the solid electrolyte and fired, or a layer of fine particles and an electrode film are applied on the solid electrolyte in this order and fired simultaneously.

Incidentally, fine particles of Au or an Au alloy have an average particle size of 0.01–10 m, preferably 0.01–1 m, more preferably 0.01–0.1 m. The shapes of particles are not necessarily spherical and may be granules or, for instance, rugby-ball shaped.

Any kind of glass material may be used in combination with gold or a gold alloy upon producing the detecting electrode, as long as it melts at a temperature which is the same as or lower than the melting point of gold or a gold alloy, and lead brosilicate glass is suitably used.

By using a glass component in combination with gold or a gold alloy, a glass phase is precipitated on interfaces among the gas phase, the metal electrode, and the solid electrolyte, thereby further suppressing a reaction of an inflammable gas, such as CO. Therefore, interferential influence caused by inflammable gas can be reduced.

Further, adhesion between a substrate made of solid electrolyte and a detecting electrode is improved.

Figure 9:
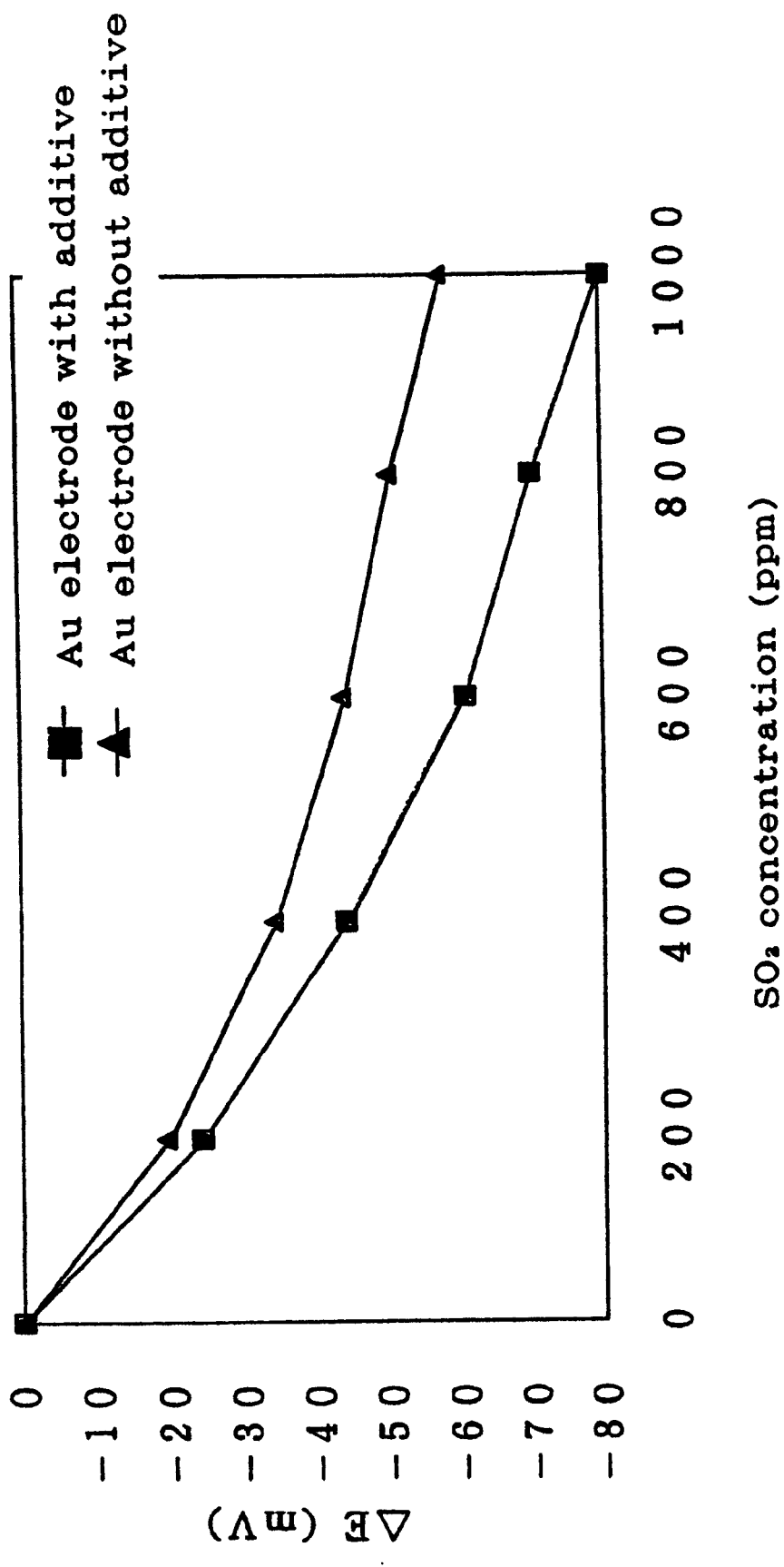
FIG. 9 is a graph showing an improvement of sensitivity of detecting $SO_2$ gas by a $SO_2$ gas detecting electrode of the present invention.

Improvement of detection sensitivity by addition of a glass component was tested in comparison with a detecting electrode having only an Au electrode. Gases containing sulfur dioxide of 0, 200, 400, 600, 800, or 1000 ppm were used for testing sensitivity of detecting sulfur dioxide. The results are shown in FIG. 9. As is clear from the results, the use of a glass component improves sensitivity of detecting sulfur dioxide.

Figure 10:
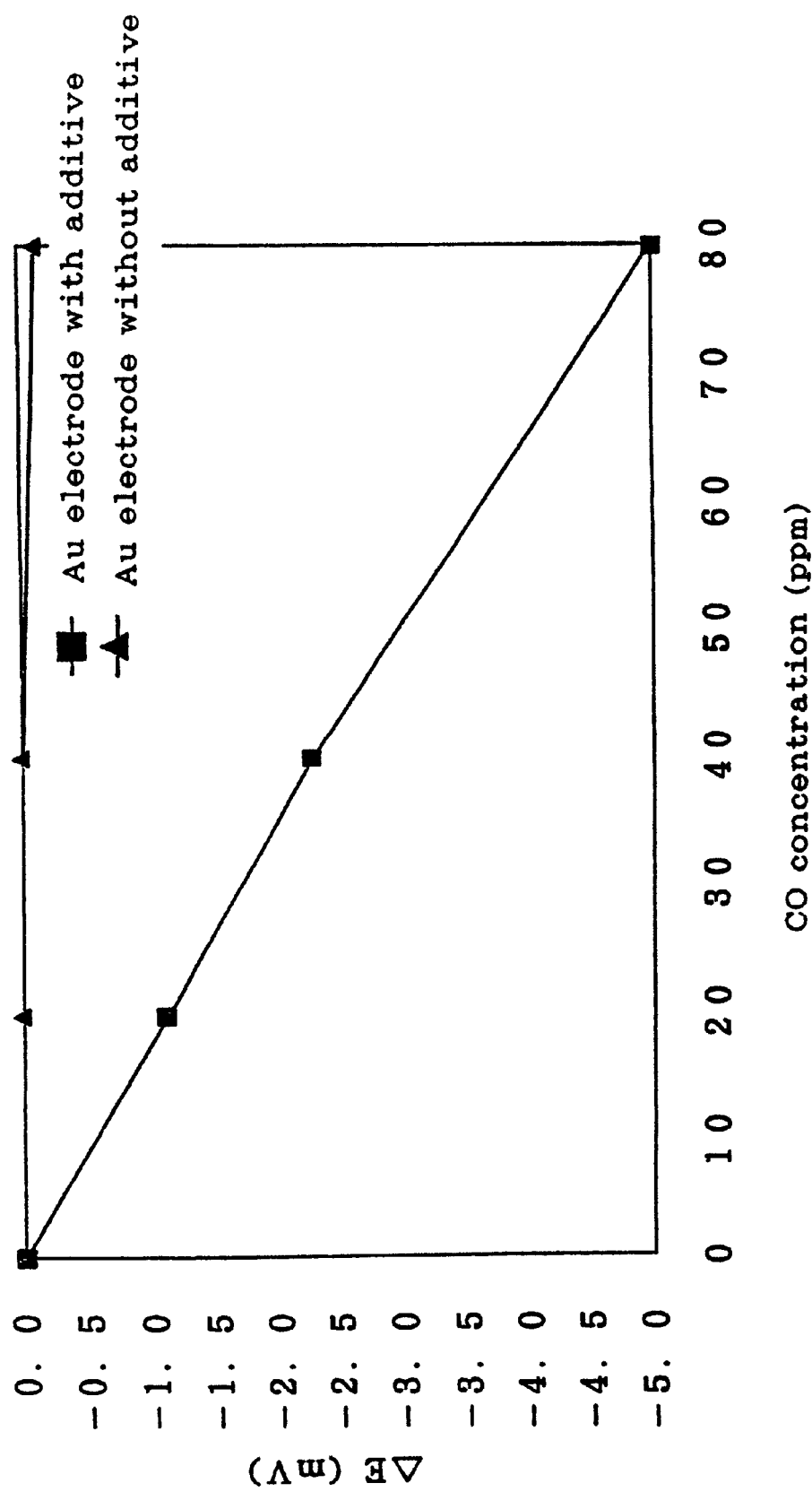
FIG. 10 is a graph showing an influence of a CO gas concentration in a gas to be measured on a $SO_2$ gas detecting electrode of the present invention.

In order to test the influence of carbon monoxide on a sulfur-dioxide detecting electrode of the present invention, a detecting electrode of the present invention and a detecting electrode made of only Au without any glass component are tested for an influence on sulfur dioxide by the use of gases containing CO gas of 0, 20, 40, or 80 ppm. The results are shown in FIG. 10. As is clear from the results, even if 80 ppm of carbon monoxide is contained in a gas to be measured, there was no influence substantially in the case of the detecting electrode of the present invention.

Incidentally, in the case of using a glass component, an amount of a glass component to be added to a sulfur dioxide detecting electrode of the present invention can be selected arbitrarily within the range of 1–10 wt % of the total weight of gold or gold alloy and the glass component.

A detecting electrode can be formed by applying a paste made of a mixed powder, gold or gold alloy, and a glass component on a substrate made of solid electrolyte and then by firing the paste. Alternatively, the mixed powder is dispersed in an adequate solvent to obtain a dispersed liquid, and the dispersed liquid is applied on the substrate made of solid electrolyte and fired.

When the amount of a glass component to be added is less than 1%, adhesion of the detecting electrode to the substrate made of solid electrolyte is not improved, and the effect of reducing interferential influence caused by inflammable gas, for example, CO is not sufficient. When it exceeds 10%, it is not preferable because delay in response or deterioration in $SO_2$ sensitivity is perceptible. A content (wt/wt %) of lead oxide in glass component has an influence on the sensing property and responding property for detecting $SO_2$ gas. A content (wt/wt %) of lead oxide in a glass component is 60 (wt/wt) % or more, preferably 60% or more and 90% or less. When it is less than 60%, delay in response is found, although influence on $SO_2$ sensitivity is not found. When it exceeds 90%, sensitivity to inflammable gas, for example, CO gas becomes slightly higher, although the $SO_2$ sensing property and responding property are not influenced. Therefore, precision in measuring $SO_2$ gas is unpreferably influenced.

The lead 5 can be fixed to the detecting electrode 3 by the use of a paste, as a material for an electrode, containing Au or an Au alloy or cermet of Au and a solid electrolyte, an Au mesh or an Au alloy mesh, and an Au lead 5 as in the aforementioned case of the basic electrode 2.

The solid electrolyte 1 to which an electrode was thus fixed is pressed to the substrate 6 so as to engage with the substrate 6. The solid electrolyte 1 functions as a partition wall separating the atmosphere of the basic gas from the atmosphere of gas to be measured. For sealing the solid electrolyte plate 1 and the substrate 5, a glass melting agent, or the like is used. As a standard gas, air is usually employed. When such a partition-type structure is employed, the $SO_2$ gas concentration in the gas to be measured can be measured by measuring electromotive due to a difference in $SO_2$ gas partial pressure between the standard gas and the gas to be measured. In this case, the basic electrode 2 may be made of the same material as the detecting electrode 3.

Figure 2:
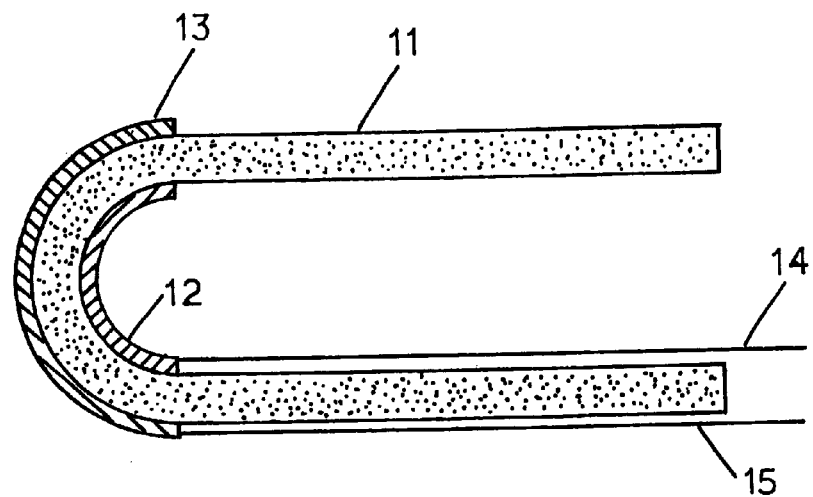
FIG. 2 is a sectional view showing an embodiment of a $SO_2$ gas sensor of the present invention.

FIG. 2 shows another embodiment of the present invention. A solid electrolyte substrate 11 having a bottomed cylindrical shape is provided with a basic electrode 12 inside and a detecting electrode 13 outside the end portion. A Pt lead 14 and a Au lead 15 are connected to the electrodes 12 and 13, respectively. The solid electrolyte substrate 11 having a bottomed cylindrical shape can be easily produced by firing a compact obtained by slip casting, extrusion molding, or injection molding. Each electrode can be produced by applying a paste, or the like, containing an electrode material on the position where an electrode is fixed to, abutting a mesh of an electrode material, and firing as in the description of the embodiment in FIG. 1. Since the embodiment also shows a structure which separates a gas to be measured and a basic gas, the sensor constitutes a concentration cell. Therefore, the basic electrode 12 may be composed of a material of Au or an Au alloy as well as the detecting electrode 13.

Figure 3:
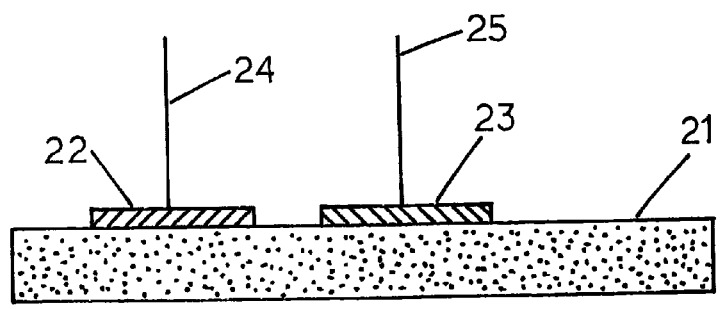
FIG. 3 is a sectional view showing another embodiment of a $SO_2$ gas sensor of the present invention.

FIG. 3 shows still another embodiment of the present invention. A basic electrode 22 and a detecting electrode 23 are fixed to the same surface of the solid electrolyte plate 21. To the basic electrode 22 and the detecting electrode 23 are fixed a Pt lead 24 and a Au lead 25. In this case, the standard gas is not required, and the whole sensor element is placed in an atmosphere for a gas to be measured. A shape of the solid electrolyte plate 21 is not limited to be laminar, and it may be any shape, for example, a cylinder or a stick.

In the case of this embodiment, the basic electrode 22 is preferably made of a material different from that of the detecting electrode 23. This is because the $SO_2$ gas concentration in the gas to be measured can be measured by measuring the electromotive force caused by the difference in electrode reaction of $SO_2$ gas between the detecting electrode 23 and the basic electrode.

Figure 4:
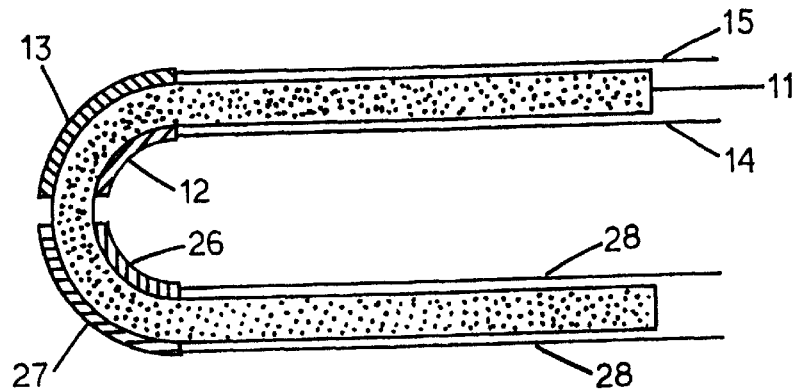
FIG. 4 is a sectional view showing an embodiment of a $SO_2$ gas sensor of the present invention, which is provided with an electrode for measuring $O_2$.

FIG. 4 shows an $SO_2$ sensor according to the present invention regarding a mode for measuring $SO_2$ gas concentration. For example, an electrode for measuring $O_2$ is fixed to an embodiment shown in FIG. 2. $SO_2$ gas concentration and $O_2$ gas concentration are simultaneously measured, thereby removing and amending influence caused by the reaction of $O_2$ which occurs as a result of measuring $SO_2$ gas by the use of the result of the measurement of $O_2$ gas concentration. Thus, $SO_2$ gas concentration can be measured independently. In this mode, there can be used the same basic electrode 12 and detecting electrode 13 for measuring $SO_2$ gas as the basic electrode and detecting electrode used in the mode shown in FIG. 2. The basic electrode 26 and the detecting electrode 27 for measuring $O_2$ are basically $O_2$ sensors. Therefore, there is preferably used a porous Pt electrode, which is used as an electrode of a conventional zirconia $O_2$ sensor. Fixing of these electrodes and a lead 28 can be performed in the same manner as in the case of the electrodes for measuring $SO_2$ gas. As a lead 28, there can be preferably used a Pt wire. Incidentally, it can be easily thought that this mode can be applied to a planar element shown in FIG. 1. A basic electrode for measuring $SO_2$ gas may be used in combination with a basic electrode for measuring $O_2$.

Figure 5:
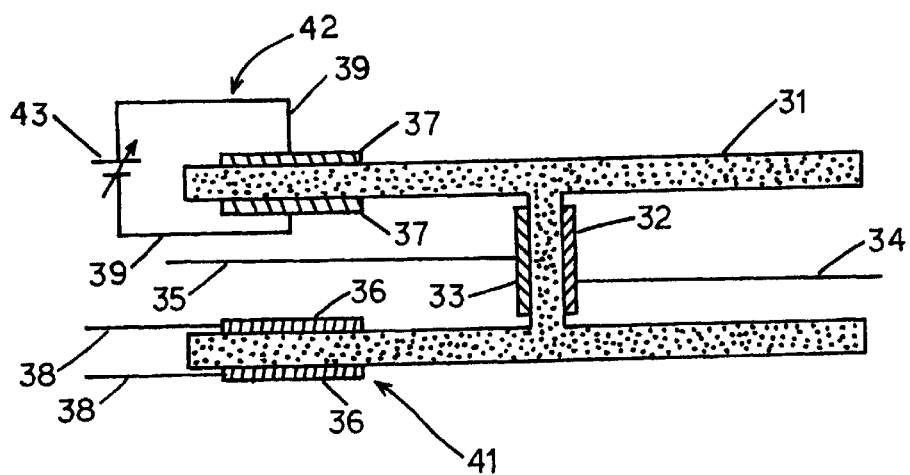
FIG. 5 is a sectional view showing an embodiment of a $SO_2$ gas sensor of the present invention, which is provided with an $O_2$ pump.

FIG. 5 shows an embodiment of sensor using an H-type electrolyte substrate 3 having two depressions. One depression contacts an atmosphere for a basic gas. At the bottom of the depression, a basic electrode 32 made of porous Pt is formed. To the basic electrode 32 is fixed a Pt lead 34. Another depression contacts an atmosphere for a gas to be measured. At the bottom of the protrusion is provided a detecting electrode 33 of Au or an Au alloy and a glass component. An Au lead 35 is fixed to the detecting electrode 33. To the side wall of the depression are fixed an $O_2$ sensor 41 and a $O_2$ pump cell 42. One of two electrodes 36 of the $O_2$ sensor 41 and one of two electrodes 37 of the $O_2$ pump cell 42 are formed inside the depression, and the other electrodes are formed outside the depression. All the electrodes contact an atmosphere for a gas to be measured. The electrode 37 of the $O_2$ pump cell preferably has a characteristic of not oxidizing $SO_2$ gas, and an electrode of a conductive metal oxide such as lanthanum manganite is preferably used.

Incidentally, as leads 38 and 39 fixed to the electrodes 37 and 38, respectively, Pt wires are preferably used. Since the electrode 37 is a ceramic electrode, a lead 39 cannot be fixed directly by welding. Therefore, generally, a surface of the electrode is metallized, and then the lead 39 is baked.

This structure enables an $O_2$ pump cell to be driven by controlling a potentiostat 43 so that $O_2$ concentration in an atmosphere in a gas to be measured is always kept constant by an $O_2$ measuring sensor. Therefore, the $O_2$ concentration is kept constant in an $SO_2$ gas detecting electrode in a gas to be measured, and it is possible to measure $SO_2$ by easily excluding the $O_2$ influence generated by a detecting electrode 33 for measuring $SO_2$ gas to be measured. Thus, measurement precision is further sought.

Figure 6:
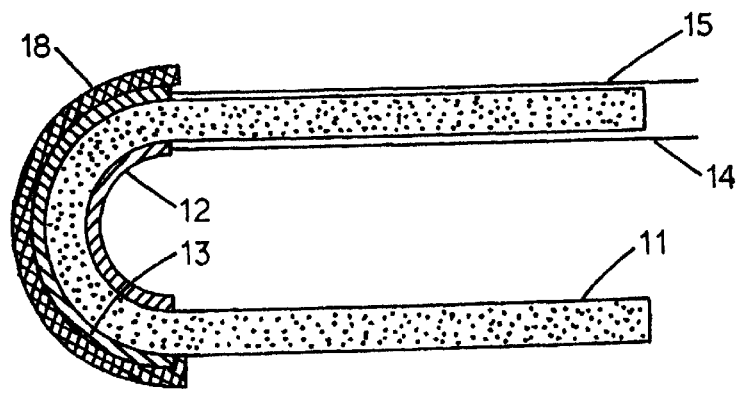
FIG. 6 is a sectional view showing an embodiment of a $SO_2$ gas sensor of the present invention, which is provided with a gas diffusion rate-determining layer.

FIG. 6 shows a structure in which a gas diffusion rate-determining layer 18 is disposed on the surface of a detecting electrode 13 for detecting $SO_2$ in a mode shown in FIG. 2. The gas diffusion rate-determining layer 18 can remove inflammable gases such as propane and butane (except for $SO_2$ gas) sent to the surface of the detecting electrode 13. Selectivity of $SO_2$ gas in a sensor of the present invention can be improved by using such a gas diffusion rate-determining layer 18. Specifically, a zeolite film is used. It can be formed by superposing the film on a surface of the detecting electrode 13 by dipping, or the like, to form a laminate. Alternatively, the gas diffusion rate-determining layer 18 can be formed by a screen printing, or the like, after the detecting electrode 13 is formed on the solid electrolyte substrate 11. It is needless to say that such a gas diffusion rate-determining layer 18 can be applied to all the aforementioned embodiments.

Regarding the aforementioned method for measuring $SO_2$ gas concentration in a $SO_2$ gas sensor, a concentration cell is formed in a structure in which a solid electrolyte plate serves as a partition to separate an atmosphere for a standard gas and an atmosphere for a gas to be measured. Therefore, $SO_2$ gas concentration can be measured by an electromotive force of the concentration cell. When the whole solid electrolyte having a detecting electrode and a basic electrode is disposed in an atmosphere for a gas to be measured, the detecting electrode for measuring $SO_2$ gas is made of a material different from that for the basic electrode. Therefore, by measuring a difference in electromotive force generated between each electrode, the $SO_2$ concentration can be known.

Additionally, in the present invention, a certain current is applied between the detecting electrode and the basic electrode for measuring $SO_2$ gas in all of the aforementioned embodiments. $SO_2$ gas can be measured by measuring a change of electromotive force due to adsorption/oxidation of $SO_2$ gas on the detecting electrode. According to this method, oxidation reaction of $SO_2$ on the electrode is promoted, and sensitivity of a sensor to $SO_2$ gas is improved. Further, a similar effect can be obtained by measuring the current, between the detecting electrode and the basic electrode, which is required in order to keep the voltage constant between the detecting electrode and the basic electrode for measuring $SO_2$ gas.

Figure 7:
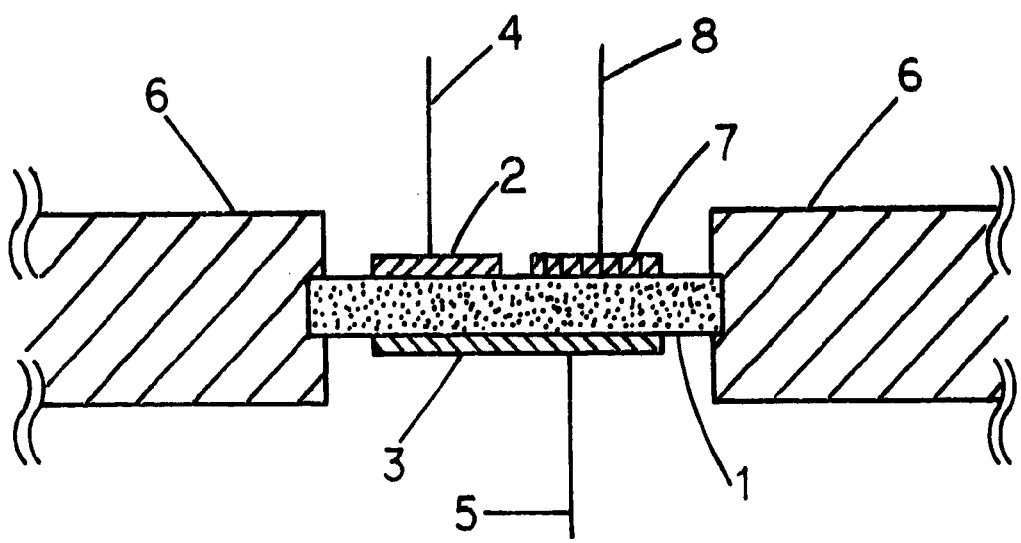
FIG. 7 is a sectional view showing an embodiment of a $SO_2$ gas sensor of the present invention, which is provided with a reference electrode.

FIG. 7 shows a structure in which a reference electrode 7 for measuring $SO_2$ gas is disposed on a $SO_2$ gas sensor shown in FIG. 1. The reference electrode 7 is made of porous Pt as in the basic electrode 2, and a Pt wire is used as a lead 8. In a $SO_2$ gas sensor of this structure, the $SO_2$ gas reaction at the detecting electrode 3 can be separately measured by measuring voltage between the reference electrode 7 and the detecting electrode 3 when a certain current is applied between the basic electrode 2 and the detecting electrode 3. This enables more precise measurement.

Figure 8:
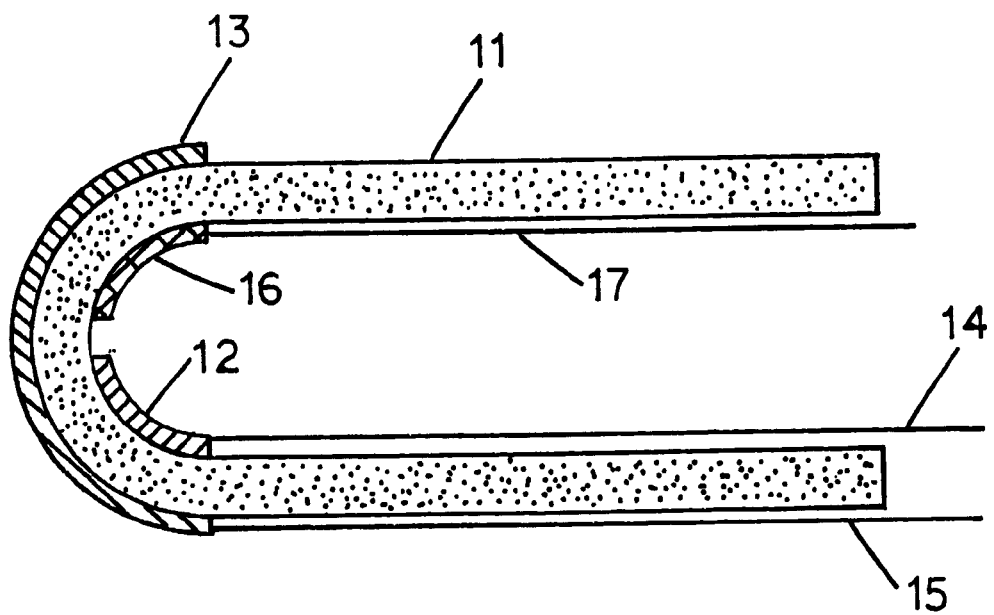
FIG. 8 is a sectional view showing another embodiment of a $SO_2$ gas sensor of the present invention, which is provided with a reference electrode.

FIG. 8 shows an embodiment in which a reference electrode 16 with a Pt lead 17 is disposed on the embodiment using the solid electrolyte substrate 11 having a bottomed cylindrical shape shown in FIG. 2. The reference electrode 16 has the same function as the reference electrode 7 shown in FIG. 7.

FIG. 9 shows results of measuring $SO_2$ gas concentration by the use of a sensor in which an electrode is made of Au without using any glass component in contrast with a sensor of the present invention. A sensor of the present invention apparently has high sensitivity in detecting $SO_2$ gas and shows that it is excellent as an $SO_2$ gas sensor.

FIG. 10 shows results of testing the influence of CO gas, which is one of the inflammable gases contained in the gas to be measured, on a sensor by the use of a sensor in which an electrode is made of Au without using any glass component in contrast with a sensor of the present invention. Influence of CO gas on a sensor of the present invention was not found substantially even with concentration of 80 PPM.

Figure 11:
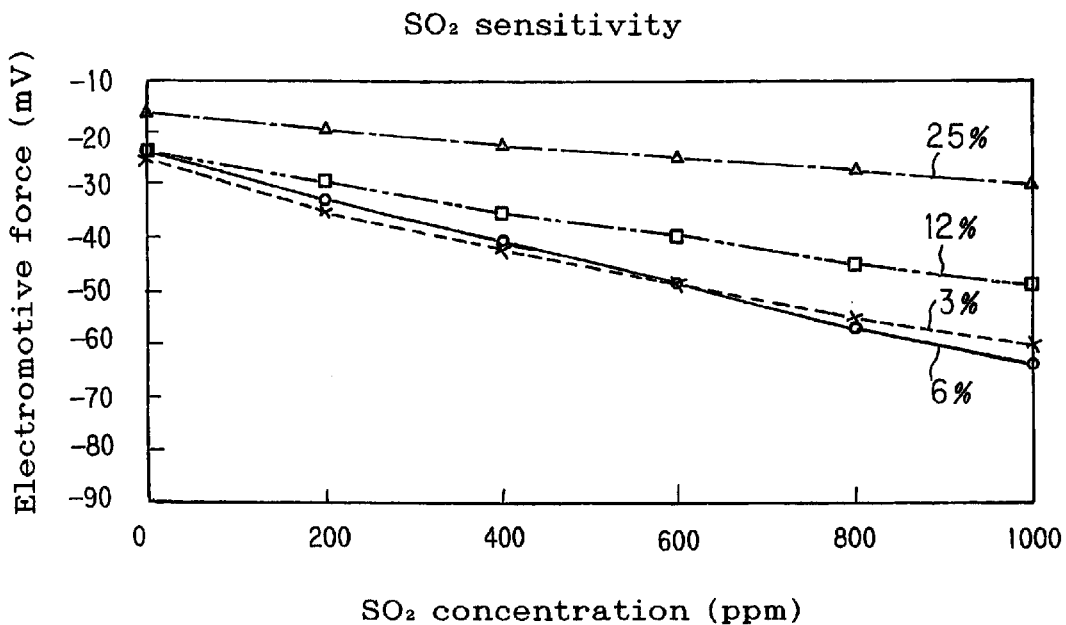
FIG. 11 is a graph showing the influence of the amount of a glass component added to Au (or Au alloy) on $SO_2$ gas detecting sensitivity.

FIG. 11 is a graph showing the influence on sensitivity of detecting $SO_2$ when a glass component of 3, 6, 12, or 25 (wt/wt) % was added to Au (or an Au alloy). This graph shows that $SO_2$ sensitivity is lowered when a glass component exceeds 10%.

Figure 12:
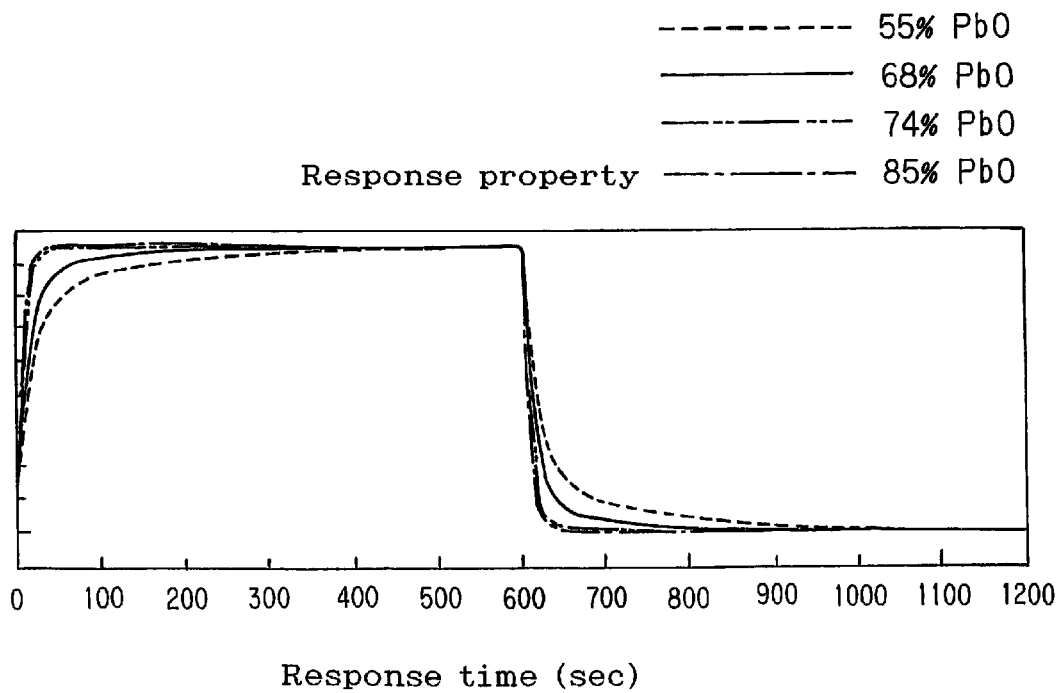
FIG. 12 is a graph showing the influence of a content of lead oxide in a glass component on a responding property.

FIG. 12 is a graph showing the influence on response properties when the lead oxide content in a glass component is controlled to be 55, 68, 74 or 85 (wt/wt) %. This graph shows that the response is slow when the content is less than 60%.

Figure 13:
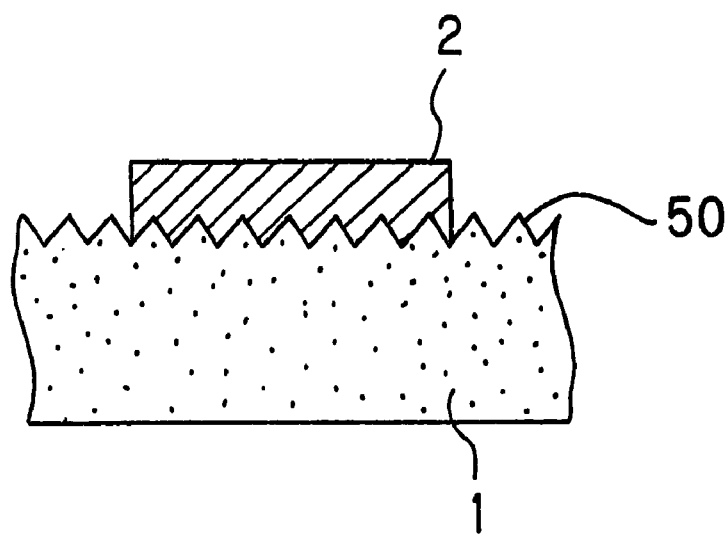
FIG. 13 is a schematic sectional view showing the state of the bonding portion between a $SO_2$ gas detecting electrode and a solid electrode which is formed after roughening a surface, on the side of the $SO_2$ gas detecting electrode to be mounted, of the solid electrode according to a method for forming a $SO_2$ gas detecting electrode of the present invention.

FIG. 13 shows a mode of a method for forming an $SO_2$ detecting electrode of the present invention.

Figure 14:
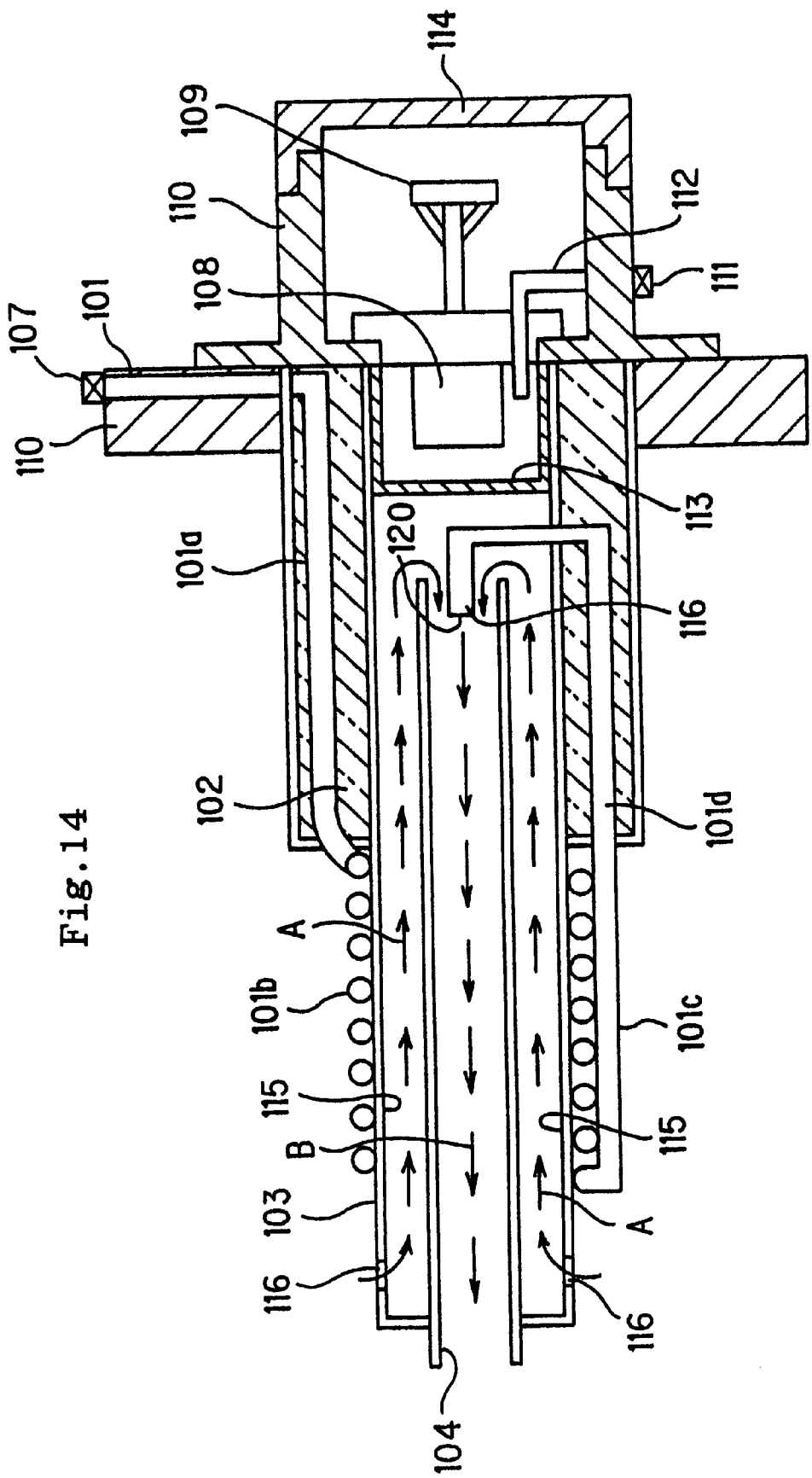
FIG. 14 is a sectional view of a $SO_2$ gas measuring apparatus on which a gas sensor of the present invention is mounted.

FIG. 14 shows a schematic view of a basic structure of a direct-coupled $SO_2$ gas measurement apparatus on which a $SO_2$ gas sensor shown in FIG. 1. This apparatus is composed basically of a sensor case 110 having a portion 118 for fixing a sensor apparatus, a sensor cover 114 fixed to the sensor case 110 so that it is attachable and detachable, a $SO_2$ gas sensor 108 of the present invention installed in a sensor box, a holder 109 to which the sensor 108 is fixed, a pipe 12 for supplying a basic gas, a filter 113 disposed on a front surface of the sensor 108 and made of porous ceramic, a pipe 103 for collecting a gas to be measured, having a dual structure, and a pipe 101 for supplying an ejector gas.

The pipe 103 for collecting the gas to be measured has a dual structure. A path 115 for collecting the gas to be measured is formed in a peripheral portion of the pipe 103, and a path 104 for discharging a gas to be measured is formed inside the pipe 103.

An ejector supply port 107 is formed at one end of the pipe 101 for supplying an ejector gas. The pipe 101 for supplying an ejector gas first passes through a heat-insulating material 102 as shown in 101a, and then reaches an exposed portion of a pipe 101b for supplying an ejector gas, which is spirally wound around the periphery of the pipe 103 for collecting a gas to be measured and has a dual structure. Then, it is connected to an exposed portion of a linear pipe 101c for supplying an ejector gas and passes through the heat-insulating material 102. Then, it is exposed to inside of the pipe 103 and connected to an ejector 106.

When an ejector gas is supplied from the ejector supply port 107, the ejector gas passes through an embedded portion 101a in the heat-insulating material 102, and the exposed portion 101b and 101c and an embedded portion 101d in the heat-insulating material 102 in this order and spouts out of the ejector discharge port 120. This reduces pressure in a periphery of the ejector 106 and causes a convection. As a result, the gas to be measured is collected from outside of the apparatus via a collection port 116 and flows along an arrow A in a path 115 for collecting a gas to be measured. The gas reverses to flow along an arrow B in a path 104 for discharging a gas to be measured, and is discharged outside of the apparatus. Meanwhile, $SO_2$ gas in the gas to be measured is measured by a sensor 108.

As described above, according to an $SO_2$ gas sensor of the present invention, when an $SO_2$ gas concentration in an exhaust gas discharged from various kinds of combustion engines in thermoelectric power plants, incineration facilities, or the like, or in the air, selectivity of $SO_2$ gas can be improved by employing an electrode containing Au or an Au alloy, which has a lower catalytic ability to $SO_2$ gas than Pt, which has conventionally been used, and a glass component for the detecting electrode for measuring $SO_2$ gas. Further, precision in measuring $SO_2$ gas is improved by compensating a value of $SO_2$ gas measurement by a value of an $O_2$ gas measurement by the use of $O_2$ sensor in combination. Particularly, even if an oxygen gas coexists in an exhaust gas, influence of $O_2$ concentration on a value of $SO_2$ gas concentration measurement can be made very small. Additionally, in all the $SO_2$ gas sensors of the present invention, sensitivity to $SO_2$ gas can be improved by applying a certain current between electrodes for measuring $SO_2$ gas or by keeping a voltage constant. Generally, precision in $SO_2$ gas sensor can be remarkably improved. Further, an area of contact interfaces among a gas phase, a metal electrode, and a solid electrolyte can be enlarged by making rough a surface, on the side of the detecting electrode, of the solid electrolyte by a chemical etching, or the like, or by disposing a layer of a fine particles of gold or gold alloy between the solid electrolyte and the electrode film. Since the sensor can be operated at the high temperature of 600° C.–900° C., an error caused by other interferential gas components contained in a gas to be measured is decreased.

What is claimed is:

1. A sulfur dioxide gas sensor comprising:

a solid electrolyte having oxygen ion conductivity;

a detecting electrode for measuring sulfur dioxide gas, electrically connected to at least a part of a surface of the solid electrolyte; and a basic electrode for measuring sulfur dioxide gas, electrically connected to at least a part of a surface of the solid electrolyte;

wherein the detecting electrode contains (a) either gold or a gold alloy comprising 90 wt. % or more gold for measuring sulfur dioxide gas, and (b) glass containing lead oxide of 60% or more and in an amount of 1 to 10 weight % based on the weight of the gold or gold alloy.

2. A sulfur dioxide gas sensor according to claim 1, wherein both the detecting electrode for measuring sulfur dioxide gas and the basic electrode for measuring sulfur dioxide gas are disposed on the same surface of the solid electrolyte.

3. A sulfur dioxide gas sensor according to claim 1, wherein a reference electrode for measuring sulfur dioxide gas is employed next to the detecting electrode for measuring sulfur dioxide gas and the basic electrode for measuring sulfur dioxide gas so as to give a three-electrode structure.

4. A sulfur dioxide gas sensor according to claim 3, further comprising means for measuring the sulfur dioxide gas content which comprises means for applying a certain current between the detecting electrode for measuring sulfur dioxide and the basic electrode for measuring sulfur dioxide and means for measuring the resulting change of electromotive force between the detecting electrode and the reference electrode caused by adsorption/oxidation of sulfur dioxide gas in the detecting electrode for measuring sulfur dioxide gas.

5. A sulfur dioxide gas sensor according to claim 3, further comprising means for measuring the sulfur dioxide content which comprises means for maintaining a certain voltage between the detecting electrode for measuring sulfur dioxide and the basic electrode for measuring sulfur dioxide and means for measuring amperage between the detecting electrode for measuring sulfur dioxide gas and the reference electrode for measuring sulfur dioxide gas by an oxidation reaction of sulfur dioxide gas in the detecting electrode for measuring sulfur dioxide gas.

6. A sulfur dioxide gas sensor according to claim 1, further comprising means for measuring the sulfur dioxide gas content which comprises means for applying a certain current between the detecting electrode for measuring sulfur dioxide and the basic electrode for measuring sulfur dioxide and means for measuring the resulting change of electromotive force caused by adsorption/oxidation of sulfur dioxide gas in the detecting electrode for measuring sulfur dioxide gas.

7. A sulfur dioxide gas sensor according to claim 1, further comprising means for measuring the sulfur dioxide content which comprises means for maintaining a certain voltage between the detecting electrode for measuring sulfur dioxide and the basic electrode for measuring sulfur dioxide and means for measuring a change in amperage by an oxidation reaction of sulfur dioxide gas in the detecting electrode for measuring sulfur dioxide gas.

8. A sulfur dioxide gas sensor according to claim 1, wherein the solid electrolyte comprises zirconium oxide and a stabilizer.

9. A sulfur dioxide gas sensor according to claim 8, wherein the stabilizer contained in the solid electrolyte includes at least one of; magnesium oxide, calcium oxide, yttrium oxide, cerium oxide, scandium oxide, and rare earth metal oxides.

10. A sulfur dioxide gas sensor according to claim 1, wherein the solid electrolyte is made of a material which is capable of operating at temperatures ranging from 600° C.–900° C.

11. A sulfur dioxide gas sensor according to claim 1, wherein the gold alloy comprises 95 wt. % or more gold.

12. A sulfur dioxide gas sensor according to claim 11, wherein the gold alloy comprises 99 wt. % or more gold.

13. A sulfur dioxide gas sensor comprising:
   a solid electrolyte having oxygen ion conductivity;
   a detecting electrode for measuring sulfur dioxide gas, electrically connected to at least a part of a surface of the solid electrolyte;
   a basic electrode for measuring sulfur dioxide gas, electrically connected to at least a part of a surface of the solid electrolyte; and
   a detecting electrode for measuring oxygen and/or a basic electrode for measuring oxygen;
   wherein the detecting electrode for measuring sulfur dioxide gas contains glass and either gold or a gold alloy.

14. A sulfur dioxide gas sensor comprising:
   a solid electrolyte having oxygen ion conductivity;
   a detecting electrode for measuring sulfur dioxide gas, electrically connected to at least a part of a surface of the solid electrolyte;
   a basic electrode for measuring sulfur dioxide gas, electrically connected to at least a part of a surface of the solid electrolyte;
   a detecting electrode for measuring oxygen and/or a basic electrode for measuring oxygen; and
   an oxygen pump cell for controlling oxygen content in an atmosphere for measurement;
   wherein the detecting electrode for measuring sulfur dioxide gas contains glass and either gold or a gold alloy.

15. A sulfur dioxide gas sensor according to claim 14, wherein an electrode for the oxygen pump cell is a metal oxide.

16. A sulfur dioxide gas sensor according to claim 14, wherein both the detecting electrode for measuring sulfur dioxide gas and the basic electrode for measuring sulfur dioxide gas are disposed on the same surface of the solid electrolyte.

17. A sulfur dioxide gas sensor according to claim 14, wherein a reference electrode for measuring sulfur dioxide gas is employed next to the detecting electrode for measuring sulfur dioxide gas and the basic electrode for measuring sulfur dioxide gas so as to make a three-electrode structure.

18. A sulfur dioxide gas sensor according to claim 14, further comprising measuring means for simultaneously measuring the sulfur dioxide gas content and the oxygen content and means for determining the sulfur dioxide gas content by utilizing the measurement of the sulfur dioxide gas content and the measurement of the oxygen content.

* * * * *